United States Patent [19]

Franz et al.

[11] Patent Number: 4,652,297

[45] Date of Patent: Mar. 24, 1987

[54] HYDRAZIDO DERIVATIVES OF N-PHOSPHINOTHIOYLMETHYLGLYCINE ESTERS

[75] Inventors: John E. Franz, Crestwood; Robert J. Kaufman, University City, both of Mo.

[73] Assignee: Monsanto Company, St. Louis, Mo.

[21] Appl. No.: 352,401

[22] Filed: Feb. 25, 1982

Related U.S. Application Data

[63] Continuation of Ser. No. 107,208, Dec. 26, 1979, abandoned.

[51] Int. Cl.$^4$ .................... A01N 57/10; A01N 57/16; C07C 149/20
[52] U.S. Cl. .......................... 71/87; 560/147; 544/129; 544/141; 544/157; 546/186; 546/208; 546/209; 546/223; 546/244; 548/413
[58] Field of Search ...................... 71/87, 86; 560/147, 560/155, 169

[56] References Cited

U.S. PATENT DOCUMENTS 3,799,758  3/1974  Franz ..................................... 71/86
4,067,719  1/1978  Dutra ..................................... 71/86

*Primary Examiner*—Catherine L. Mills
*Attorney, Agent, or Firm*—David Bennett; William H. Duffey; Arnold H. Cole

[57] ABSTRACT

This invention relates to a new class of organic chemical compounds. More particularly, this invention is concerned with amido and hydrazido derivatives of N-phosphinothioylmethylglycine esters. This class of compounds has been found to be useful as herbicides.

9 Claims, No Drawings

HYDRAZIDO DERIVATIVES OF N-PHOSPHINOTHIOYLMETHYLGLYCINE ESTERS

This is a continuation of Ser. No. 107,208 filed Dec. 26, 1979, now abandoned.

This invention relates to a new class of organic chemical compounds. More particularly, this invention is concerned with amido and hydrazido derivatives of N-phosphinothioylmethylglycine esters wherein amido or hydrazido groups are bonded to the phosphorus atom in addition to a divalent sulfur atom. This class of compounds has been found to display desirable herbicidal activity when applied to certain varieties of weeds or undesired plants.

U.S. Pat. No. 3,799,758 describes the preparation of N-phosphonomethylglycine and certain of its esters, amides and salts. Also described is the use of such compounds as contact or post-emergent herbicides.

*Biomedical Mass Spectrometry*, Vol. 3, (1976) pages 28–31 describes the tributyl ester derivatives of N-trifluoroacetyl-N-phosphonomethylglycine.

It will be apparent from a study of the above patents and publication that none of them disclose or suggest amido or hydrazido N-phosphonomethylglycine esters containing a P=S grouping.

The compounds of the present invention are represented by the formula

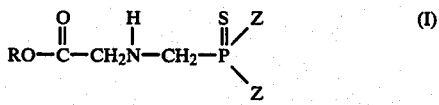
(I)

wherein R is a member of the class consisting of alkyl of from 1 to 8 carbon atoms, chloroalkyl of from 1 to 4 carbon atoms and from 1 to 3 chlorine atoms and alkoxyalkyl containing from 3 to 7 carbon atoms and wherein Z is a member of the class consisting of

wherein each R' is individually selected from the class consisting of hydrogen, $C_1$–$C_4$ alkyl, $C_2$–$C_4$ alkenyl, $C_3$–$C_7$ cycloalkyl, benzyl or phenyl; a heterocyclic group selected from the class consisting of morpholine, pyrrolidine or piperidine; or a

group wherein $Z_1$ is a

group wherein R" is hydrogen, $C_1$–$C_4$ alkyl or phenyl; a heterocyclic group selected from the class consisting of piperidine, pyrrolidine and morpholine. It is preferred that R be alkyl or chloroalkyl of from 1 to 4 carbon atoms. It is even more preferred that R be methyl or ethyl. It is preferred that Z represent alkylamino or dialkylamino of from 1 to 4 carbon atoms.

Illustrative of the alkyl groups represented by R are methyl, ethyl, n- and isopropyl, n-, sec, iso- and tert-butyl, pentyl, hexyl and octyl. The chloroalkyl groups that R represents are, for example, chloromethyl, chloroethyl, chloropropyl, trichloropropyl, chlorobutyl and the like.

Illustrative of the alkoxyalkyl groups which R represents are methoxyethyl, methoxypropyl, methoxybutyl, ethoxyethyl, ethoxypropyl, propoxyethyl, propoxypropyl and the like.

Illustrative of the alkyl groups represented by R' and R" are methyl, ethyl, propyl, butyl, isobutyl and the like. Illustrative of the alkenyl groups represented by R' are vinyl, allyl, butenyl and the like. Illustrative of the cycloalkyl groups represented by R' are, for example, cyclopropyl, cyclobutyl, cyclopentyl, cyclohexyl and cycloheptyl.

In accordance with the present invention, the compounds of formula (I) are prepared by reacting a compound of the formula

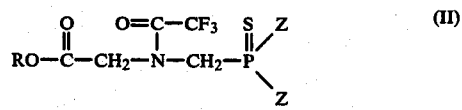
(II)

wherein R and Z are as above defined with sodium tetrahydridoboron in the presence of an aprotic solvent at a temperature of from 0° C. to about 50° C.

The above reaction is generally conducted at temperatures of from 0° C. to ambient temperature. However, temperatures in the range of from 0° C. to 50° C. can be employed. Temperatures of from 0° C. to 25° C. are preferred for convenience.

The starting materials employed in the preparation of the compounds of this invention are prepared by reacting a compound of the formula

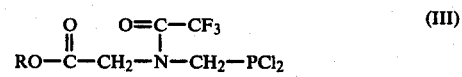
(III)

wherein R is as above defined with an amine or hydrazine of the formula

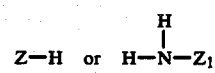

wherein Z and $Z_1$ are as above defined in the presence of a hydrogen halide acceptor and then treating the reaction mixture with at least an equivalent amount of elemental sulfur.

The above reaction is generally conducted at ambient temperature. However, temperatures in the range of from 0° C. to 50° C. can be employed. Ambient temperatures of from 15° C. to 25° C. are preferred for convenience.

If it is desired to produce compounds of formula (I) wherein each Z is different, it is necessary to perform sequential steps in amination or hydrazination with the hydrogen halide acceptor. In each instance, one equivalent of the compound of the formula

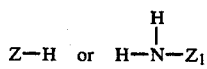

wherein Z and $Z_1$ are as above defined is added at each step.

It is, of course, apparent to those skilled in the art that for each chloro group in the compounds of formula (III), one should employ at least one equivalent of the amine or hydrazine together with at least an equivalent amount of the hydrogen halide acceptor.

Inasmuch as the dichlorophosphinyl compounds of formula (III) are unstable towards moisture, the reaction, for best results, must be conducted in an anhydrous environment, that is, anhydrous reagents and solvents should be employed. Although the reaction can be conducted in a stepwise manner, i.e., by isolating the dichloro compound of formula (III) and then conducting the amination and then subsequent conversion to the thioyl derivative, it is preferred for convenience to conduct the total reaction in a single reaction vessel without complete isolation and identification of the dichlorophosphinic compound.

The starting compounds of formula (III) employed in the production of the compounds of the invention are prepared by the following general procedure.

An ester of N-hydroxyphosphinylmethylglycine is dissolved in trifluoroacetic acid and an equal molar quantity or slight excess of trifluoroacetic anhydride is added dropwise with stirring at ambient temperature. Too large an excess of anhydride should be avoided to obtain the best yields of the compound. The reaction mixture is then concentrated in vacuo to yield the ester of N-trifluoroacetyl-N-(hydroxyphosphinylmethyl)glycine.

The ester of N-trifluoroacetyl-N-(hydroxyphosphinylmethyl)glycine is then converted to the ester of N-trifluoroacetyl-N-[bis(chloro)phosphonomethyl]glycine by dissolving in benzene and then adding to excess phosphorus trichloride at ambient temperature. The phosphine dichloride is recovered by filtration and then concentration of the filtrate in vacuo.

The dichloro phosphine compound is extremely sensitive to moisture. It is, therefore, desirable and necessary to employ anhydrous reagents and aprotic solvents while protecting the reaction mixture from moisture to obtain the best yields.

The compounds of this invention are useful as herbicides.

The following examples serve to further illustrate the invention. In the examples, all parts are parts by weight unless otherwise expressly set forth.

EXAMPLE 1

N-trifluoroacetyl-N-[bis(pyrrolidino)phosphinothioylmethyl]glycine, 2-ethoxy ethyl ester (3.85 g, 0.0083 mole), was dissolved in tetrahydrofuran (50 ml) and water (10 ml) and cooled to 0° C. on an ice bath. The solution was stirred and sodium tetrahydrido boron (318 mg, 0.0083 mole) was added portionwise over about 10 minutes. The solution was allowed to warm to room temperature and stirred for 100 minutes. The solvent was removed by evaporation under vacuum and the residue was washed with water. The water washings were saturated with sodium chloride and the aqueous layer and insoluble residue were simultaneously extracted with ethyl acetate three times. The combined ethyl acetate extracts were dried over sodium sulfate, filtered and concentrated in vacuo. The resulting residue was then chromatographed on silica gel employing ether to yield N-[bis(pyrrolidino)phosphinothioylmethyl]glycine, 2-ethoxy ethyl ester (150 mg), $N_D^{25}=1.5354$, and having the following analysis: Calculated: C, 48.32; H, 8.32; N, 11.27. Found: C, 48.38; H, 7.91; N, 11.13.

EXAMPLE 2

N-trifluoroacetyl-N-[bis(N-methyl-N-benzylamino)phosphinothioylmethyl]glycine, octyl ester (3.7 g, 6.16 mm), was dissolved in 30 ml of tetrahydrofuran containing 6 ml of water and cooled to 0° C. on an ice bath. The solution was stirred and sodium tetrahydrido boron (234 mg, 6.16 mm) was added portionwise over about 10 minutes. The solution was allowed to warm to room temperature and stirred for an additional 35 minutes. (a) The solvent was removed by evaporation under vacuum and the residue was washed with water. The water washings were saturated with sodium chloride and the aqueous layer and the insoluble residue were simultaneously extracted with ethyl acetate three times. The combined ethyl acetate extracts were dried over sodium sulfate, filtered and concentrated in vacuo. A thin layer chromatograph of the residue indicated that the starting material was still present. The remainder of this residue was dissolved in tetrahydrofuran (30 ml), $H_2O$ (6 ml) and sodium tetrahydridoboron (234 mg) was added with stirring. The solution was stirred for 2 hours. This solution was then treated as in step (a). The resulting residue from the repeat of step (a) was then chromatographed on silica gel employing ether to yield N-[bis(N-methyl-N-benzylamino)phosphinothioylmethyl]glycine, octyl ester (700 mg) having a refractive index $N_D^{25}=1.5404$.

EXAMPLE 3

N-trifluoroacetyl-N-[bis(morpholino)phosphinothioylmethyl]glycine, methyl ester (5.35 g, 0.0123 mole) was dissolved in isopropanol and cooled to 0° C. on an ice bath. The solution was stirred and sodium tetrahydrido boron (467 mg, 0.0123 mole) was added portionwise over a ten minute period. The solution was allowed to warm to room temperature and stirred for an additional 45 minutes. The solvent was removed by evaporation under vacuum and the resulting residue was washed with water. The water washings were saturated with sodium chloride and the aqueous layer and insoluble residue were simultaneously extracted with ethyl acetate three times. The combined ethyl acetate extracts were dried over sodium sulfate, filtered and concentrated in vacuo. The resulting residue was then chromatographed on silica gel employing 25% ethanol in ethyl acetate (V:V) to obtain N-[bis(morpholino)phosphinothioylmethyl]glycine, isopropyl ester (300 mg), having a refractive index $N_D^{25}=1.5205$ and the following analysis: Calculated: C, 44.33; H, 7.78; N, 11.08. Found: C, 44.83; H, 7.59; N, 10.76.

EXAMPLE 4

N-trifluoroacetyl-N-[bis(dimethylamino)phosphinothioylmethyl]glycine, ethyl ester (1 g, 0.00275 mole), was dissolved in ethanol (20 ml). The resulting solution was stirred and sodium tetrahydrido boron (0.104 g, 0.00275 mole) was added portionwise over a ten minute period. The resulting solution was stirred for 60 minutes. The solvent was removed by evaporation under vacuum and the residue was washed with water. The water washings were saturated with sodium chloride and the aqueous layer and insoluble residue were simultaneously extracted with ethyl acetate three times. The combined ethyl acetate extracts were dried over sodium sulfate, filtered and concentrated in vacuo. The resulting residue was then chromatographed on silica gel with ether to yield N-[bis(dimethylamino)phosphinothioylmethyl]glycine, ethyl ester, $N_D^{25} = 1.5317$.

EXAMPLE 5

N-trifluoroacetyl-N-[bis(2,2-dimethylhydrazino)-phosphinothioylmethyl]glycine, ethyl ester (2 g, 0.005 mole), was dissolved in ethanol. The solution was stirred and sodium tetrahydrido boron (193 mg, 0.005 mole) was added portionwise over a ten minute period. The resulting solution was stirred for 30 minutes. The solvent was removed by evaporation under vacuum and the residue was washed with water. The water was saturated with sodium chloride and the aqueous layer and insoluble residue were simultaneously extracted with ethyl acetate three times. The combined ethyl acetate extracts were dried over sodium sulfate, filtered and concentrated in vacuo to yield N-[bis(2,2-dimethylhydrazino)phosphinothioylmethyl]glycine, ethyl ester (800 mg), as a white solid, m.p. 75.5°-85° C.

EXAMPLE 6

N-trifluoroacetyl-N-[bis(ethylamino)phosphinothioylmethyl]glycine, ethyl ester (2 g, 0.0055 mole), was dissolved in ethanol. The solution was stirred and sodium tetrahydrido boron (210 mg, 0.0055 mole) was added portionwise over a ten minute period. The solution was stirred for an additional 40 minutes. The solvent was removed by evaporation under vacuum and the residue was washed with water. The water washings were saturated with sodium chloride and the aqueous layer and insoluble residue were simultaneously extracted with ethyl acetate three times. The combined ethyl acetate extracts were dried over sodium sulfate, filtered and concentrated in vacuo. The resulting residue was then chromatographed on silica gel employing dichloromethane and then ether to yield N-[bis(ethylamino)phosphinothioylmethyl]glycine, ethyl ester (300 mg), $N_D^{25} = 1.5128$ and having the following analysis: Calculated: C, 40.44; H, 8.30; N, 15.72; P, 11.59; S, 11.99. Found: C, 40.19; H, 8.06; N, 15.37; P, 11.33; S, 11.74.

EXAMPLE 7

N-trifluoroacetyl-N-[bis(pyrrolidino)phosphinothioylmethyl]glycine, ethyl ester (2.7 g, 0.00649 mole), was dissolved in ethanol. The solution was stirred and sodium tetrahydrido boron (245 mg, 6.49 mm) was added portionwise over a ten minute period. The solution was stirred for an additional 20 minutes. The solvent was removed by evaporation under vacuum and the residue was washed with water. The water washings were saturated with sodium chloride and the aqueous layer and insoluble residue were simultaneously extracted with ethyl acetate three times. The combined ethyl acetate extracts were dried over sodium sulfate, filtered and concentrated in vacuo. The resulting residue was then chromatographed on silica gel employing ether as an eluant to yield N-[bis(pyrrolidino)phosphinothioylmethyl]glycine, ethyl ester (550 mg), $N_D^{25} = 1.530$ and having the following analysis: Calculated: C, 48.88; H, 8.21; N, 13.16. Found: C, 48.65; H, 8.12; N, 13.04.

EXAMPLE 8

N-trifluoroacetyl-N-[bis(cyclohexylamino)phosphinothioylmethyl]glycine, ethyl ester (4 g, 8.49 mm), was dissolved in ethanol (40 ml). The solution was stirred and sodium tetrahydrido boron (322 mg, 8.49 mm) was added portionwise over a ten minute period. The solution was stirred for an additional 30 minutes. The solvent was removed by evaporation under vacuum and the residue was washed with water. The water washings were saturated with sodium chloride and the aqueous layer and insoluble residue were simultaneously extracted with ethyl acetate three times. The combined ethyl acetate extracts were dried over sodium sulfate, filtered and concentrated in vacuo. The residue was then chromatographed on silica gel with ether to yield N-[bis(cyclohexylamino)phosphinothioylmethyl]glycine, ethyl ester (1.3 g), m.p. 74°-90° C.

EXAMPLE 9

N-trifluoroacetyl-N-[bis(isopropylamino)phosphinothioylmethyl]glycine, ethyl ester (2 g, 5.1 mm), was dissolved in ethanol. The solution was stirred and sodium tetrahydrido boron (194 mg, 5.1 mm) was added portionwise over a ten minute period. The solution was stirred for an additional 30 minutes. The solvent was removed by evaporation under vacuum and the residue was washed with water. The water was saturated with sodium chloride and the aqueous layer and insoluble residue were simultaneously extracted with ethyl acetate three times. The combined ethyl acetate extracts were dried over sodium sulfate, filtered and concentrated in vacuo. The residue was chromatographed on silica gel employing ether as an eluant to yield N-[bis(isopropylamino)phosphinothioylmethyl]glycine, ethyl ester, as a white solid, m.p. 63° C. and having the following analysis: Calculated: C, 42.17; H, 8.90; N, 13.40; P, 9.90; S, 10.20. Found: C, 41.98; H, 8.10; N, 13.22; P, 9.39; S, 9.74.

EXAMPLE 10

N-trifluoroacetyl-N-[bis(piperidineamino)phosphinothioylmethyl]glycine, ethyl ester (4 g, 8.4 mm), was dissolved in ethanol. The solution was stirred and sodium tetrahydrido boron (320 mg, 8.4 mm) was added portionwise over a ten minute period. The solution was stirred for an additional 30 minutes. The solvent was removed by evaporation under vacuum and the residue was washed with water. The water washings were saturated with sodium chloride and the aqueous layer and insoluble residue were simultaneously extracted with ethyl acetate three times. The combined ethyl acetate extracts were dried over sodium sulfate, filtered and concentrated in vacuo. The residue was then chromatographed on silica gel employing a diethyl ether as the eluant and then acetone to yield N-[bis(piperidineamino)phosphinothioylmethyl]glycine, ethyl ester (1.6 g) as a solid, m.p. 77°-80° C. and having the following analysis: Calculated: C, 47.73; H, 8.54; N, 18.55. Found: C, 47.51; H, 8.50; N, 18.41.

EXAMPLE 11

N-trifluoroacetyl-N-[bis(diallylamino)phosphinothioylmethyl]glycine, ethyl ester (2 g, 4.2 mm), was dissolved in ethanol (40 ml). The solution was stirred and sodium tetrahydrido boron (162 mg, 4.2 mm) was added portionwise over a ten minute period. The solution was stirred for an additional 30 minutes. The solvent was removed by evaporation under vacuum and the residue was washed with water. The water washings were saturated with sodium chloride and the aqueous layer and insoluble residue were simultaneously extracted with ethyl acetate three times. The combined ethyl acetate extracts were dried over sodium sulfate, filtered and concentrated in vacuo. The resulting residue was then chromatographed on silica gel employing dichloromethane and then ether to yield N-[bis(diallylamino)phosphinothioylmethyl]glycine, ethyl ester (300 mg), as a yellow solid, m.p. 80°–82° C. and having the following analysis: Calculated: C, 54.97; H, 8.14; N, 11.31. Found: C, 54.74; H, 8.13; N, 11.25.

EXAMPLE 12

N-trifluoroacetyl-N-[bis(sec-butylamino)phosphinothioylmethyl]glycine, butyl ester (4 g, 8.9 mm), was dissolved in ethanol (30 ml) and cooled to 0° C. on an ice bath. The solution was stirred and sodium tetrahydrido boron (339 mg, 8.9 mm) was added portionwise over a ten minute period. The solution was allowed to warm to room temperature and stirred for an additional 45 minutes. The solvent was removed by evaporation under vacuum and the residue was washed with water. The water washings were saturated with sodium chloride and the aqueous layer and insoluble residue were simultaneously extracted with ethyl acetate three times. The combined ethyl acetate extracts were dried over sodium sulfate, filtered and concentrated in vacuo. The residue was then chromatographed on silica gel with 5% diethyl ether in dichloromethane (V:V) to yield N-[bis(sec-butylamino)phosphinothioylmethyl]glycine, butyl ester (750 mg), as a yellow oil; $N_D^{25}=1.708$ and having the following analysis: Calculated: C, 49.93; H, 9.70; N, 11.65. Found: C, 50.11; H, 9.49; N, 11.60.

EXAMPLE 13

The post-emergence herbicidal activity of the various compounds of this invention is demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm$^2$ absolute. The atomizer contains 6 ml. of a solution or suspension of the chemical and an amount of a cyclohexanone emulsifying agent mixture so that the spray solution or suspension contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Tables I and II is as follows:

| Plant Response | Index |
| --- | --- |
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | |
| --- | --- |
| A - Canada Thistle* | K - Barnyardgrass |
| B - Cocklebur | L - Soybean |
| C - Velvetleaf | M - Sugar Beet |
| D - Morningglory | N - Wheat |
| E - Lambsquarters | O - Rice |
| F - Smartweed | P - Sorghum |
| G - Yellow Nutsedge* | Q - Wild Buckwheat |
| H - Quackgrass* | R - Hemp Sesbania |
| I - Johnsongrass* | S - Panicum Spp |
| J - Downy Brome | T - Crabgrass |

*Established from vegetative propagules.

TABLE I

| Compound of Example No. | WAT | kg/h | A | B | C | D | E | F | G | H | I | J | K |
| --- | --- | --- | --- | --- | --- | --- | --- | --- | --- | --- | --- | --- | --- |
| 1 | 4 | 33.6 | 4 | 4 | 4 | 3 | 4 | 4 | 4 | 4 | 4 | 4 | 3 |
| 2 | 2 | 11.2 | 0 | 1 | 1 | 2 | 1 | 0 | 0 | 0 | 1 | 2 | 1 |
| 3 | 4 | 11.2 | 1 | 2 | 3 | 3 | 2 | 4 | 3 | 4 | 3 | 3 | 3 |
| 3 | 4 | 5.6 | 1 | — | 3 | 3 | — | 4 | 3 | 4 | 3 | 3 | 3 |
| 4* | 4 | 11.2 | 3 | 3 | 4 | 4 | 4 | 4 | 3 | 4 | 3 | 4 | 4 |
| 4* | 4 | 5.6 | 4 | 4 | 3 | 3 | 4 | 4 | 3 | 4 | 4 | 3 | 4 |
| 5 | 4 | 11.2 | 3 | 4 | 4 | 4 | 4 | 4 | 3 | 3 | 4 | 4 | 4 |
| 5 | 4 | 5.6 | 3 | 3 | 3 | 4 | 4 | 4 | 2 | 3 | 3 | 4 | 4 |
| 6 | 4 | 11.2 | 2 | 3 | 4 | 4 | 4 | 4 | 3 | 4 | 4 | 3 | 4 |
| 6 | 4 | 5.6 | 2 | 3 | 3 | 3 | 4 | 3 | 4 | 2 | 3 | 3 | 3 | 3 |
| 7 | 4 | 11.2 | 2 | 4 | 4 | 4 | 4 | 4 | 3 | 4 | 4 | 4 | 4 |
| 7 | 4 | 5.6 | 4 | 3 | 4 | 3 | 4 | 4 | 3 | 3 | 3 | 4 | 4 |
| 8 | 4 | 11.2 | 1 | 2 | 3 | 2 | 1 | 4 | 2 | 1 | 4 | 1 | 4 |
| 8 | 4 | 5.6 | 1 | 2 | 2 | 2 | 1 | 4 | 2 | 2 | 3 | 1 | 3 |
| 9 | 4 | 11.2 | 4 | 3 | 4 | 4 | 4 | 3 | 2 | 3 | 4 | 4 | 4 |
| 9 | 4 | 5.6 | 4 | 4 | 3 | 4 | 4 | 3 | 2 | 3 | 4 | 3 | 3 |

TABLE I-continued

| Compound of Example No. | WAT | kg/h | A | B | C | D | E | F | G | H | I | J | K |
|---|---|---|---|---|---|---|---|---|---|---|---|---|---|
| 10 | 4 | 11.2 | 4 | 4 | 4 | 3 | 4 | 3 | 3 | 3 | 3 | 3 | 4 |
| 10 | 4 | 5.6 | 4 | 4 | 2 | 3 | 3 | 3 | 2 | 2 | 2 | 1 | 3 |
| 11 | 4 | 11.2 | 1 | 1 | 1 | 1 | 1 | 2 | 2 | 1 | 1 | 0 | 2 |
| 11 | 4 | 5.6 | 0 | 1 | 1 | 1 | 4 | 2 | 1 | 0 | 1 | 1 | 2 |
| 12 | 4 | 11.2 | 1 | 2 | 4 | 2 | 4 | 4 | 3 | 3 | 4 | 2 | 4 |
| 12 | 4 | 5.6 | 2 | 3 | 4 | 2 | — | 4 | 3 | 4 | 4 | 3 | 4 |

*Formulated in tetrahydrofuran diluted just prior to application.

TABLE II

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| 3 | 4 | 5.6 | 2 | 3 | 2 | 1 | 3 | — | 3 | — | 3 | 3 | 3 | 2 | 2 | 4 | 3 | 3 |
| 3 | 4 | 1.12 | 1 | 0 | 1 | 1 | 2 | 0 | 1 | — | 0 | 1 | 1 | 1 | 1 | 3 | 2 | 3 |
| 5 | 4 | 5.6 | 4 | 4 | 4 | 4 | 4 | 3 | 4 | 3 | 4 | 4 | 4 | 2 | 4 | 4 | 4 | 4 |
| 5 | 4 | 1.12 | 3 | 3 | 3 | 4 | 3 | 2 | 2 | 2 | 2 | 4 | 3 | 1 | 3 | 4 | 4 | 4 |
| 5 | 4 | 0.28 | 1 | 4 | 1 | 1 | 3 | 2 | 1 | 2 | 4 | 2 | 3 | 0 | 3 | 3 | 2 | 2 |
| 6 | 4 | 5.6 | 3 | 3 | 4 | 3 | 4 | 4 | 3 | 4 | 2 | 3 | 4 | 3 | 4 | 4 | 4 |
| 6 | 4 | 1.12 | 1 | 1 | 2 | 1 | 3 | 2 | 1 | 3 | 2 | 1 | 3 | 2 | 2 | 4 | 3 | 3 |
| 6 | 4 | 0.28 | 0 | 1 | 1 | 1 | 1 | 2 | 1 | 2 | 0 | 4 | 2 | 0 | 1 | 1 | 2 | 3 |
| 7 | 4 | 5.6 | 3 | 4 | 4 | 4 | 4 | 4 | 4 | 3 | 4 | 4 | 4 | 4 | 4 | 4 | 4 | 4 |
| 7 | 4 | 1.12 | 2 | 1 | 2 | 1 | 3 | 2 | 1 | 2 | 1 | 2 | 2 | 1 | 2 | 3 | 3 | 3 |
| 7 | 4 | 0.28 | 1 | 0 | 1 | 0 | 3 | 1 | 0 | 1 | 0 | 0 | 0 | 0 | 1 | 4 | 1 | 2 |
| 8 | 4 | 5.6 | 2 | 1 | 4 | 2 | 4 | 3 | 3 | 2 | 1 | 4 | 3 | 2 | 2 | 4 | 4 | 4 |
| 8 | 4 | 1.12 | 1 | 1 | 2 | 1 | 2 | 2 | 1 | 2 | 1 | 3 | 2 | 2 | 2 | 3 | 4 | 4 |
| 8 | 4 | 0.28 | 0 | 1 | 1 | 1 | 2 | 2 | 1 | 1 | 0 | 2 | 1 | 1 | 1 | 2 | 2 | 3 |
| 9 | 4 | 5.6 | 3 | 3 | 4 | 4 | 4 | 4 | 4 | 3 | 3 | 4 | 4 | 4 | 4 | 4 | 4 | 4 |
| 9 | 4 | 1.12 | 1 | 3 | 2 | 2 | 2 | 2 | 1 | 2 | 1 | 1 | 2 | 1 | 1 | 4 | 3 | 2 |
| 9 | 4 | 0.28 | 0 | 0 | 0 | 1 | 1 | 1 | 0 | 1 | 0 | 1 | 1 | 0 | 1 | 1 | 1 | 2 |
| 10 | 4 | 5.6 | 4 | 4 | 4 | 4 | 4 | 4 | 4 | 4 | 4 | 4 | 4 | 4 | 4 | 4 | 4 | 4 |
| 10 | 4 | 1.12 | 2 | 2 | 1 | 1 | 3 | 3 | 3 | 2 | 1 | 4 | 3 | 1 | 3 | 4 | 3 | 4 |
| 10 | 4 | 0.28 | 0 | 0 | 0 | 0 | 2 | 2 | 0 | 1 | 0 | — | 2 | 0 | 0 | 3 | 2 | 3 |
| 12 | 4 | 5.6 | 2 | 4 | 4 | 3 | 4 | 4 | 4 | 3 | 3 | 4 | 4 | 4 | 4 | 4 | 4 | 4 |
| 12 | 4 | 1.12 | 1 | 4 | 4 | 3 | 3 | 2 | 1 | 2 | 2 | 4 | 4 | 2 | 3 | 5 | 4 | — |
| 12 | 4 | 0.28 | 1 | 0 | 1 | 0 | 2 | 2 | 1 | 1 | 2 | 4 | 4 | 1 | 1 | 4 | 3 | 3 |
| 12 | 4 | 0.056 | 0 | 0 | 1 | 0 | 0 | 0 | 0 | 0 | 0 | 0 | 0 | 0 | 0 | 2 | 2 | 2 |

EXAMPLE 14

The pre-emergent herbicidal activity of various compounds of this invention is demonstrated as follows. A good grade of top soil is placed in aluminum pans and compacted to a depth of 0.95 to 1.27 cm. from the top of each pan. A predetermined number of seeds or vegetative propagules of each of several plant species are placed on top of the soil in each pan and then pressed down. Herbicidal compositions prepared as in the previous example are applied by admixture with or incorporation in the top layer of soil.

In this method, the soil required to cover the seeds and propagules is weighed and admixed with a herbicidal composition containing a known amount of the active ingredient (compound of this invention). The pans are then filled with the admixture and leveled. Watering is carried out by permitting the soil in the pans to absorb moisture through apertures in the pan bottoms. The seed and propagule containing pans are placed on a wet sand bench and maintained for approximately two weeks under ordinary conditions of sunlight and watering. At the end of this period, the number of emerged plants of each species is noted and compared to an untreated control. The data is given in Table III.

The pre-emergent herbicidal activity index used below is based upon average percent control of each species as follows:

| Percent Control | Index |
|---|---|
| 0-24% control | 0 |
| 25-49% control | 1 |
| 50-74% control | 2 |
| 75-100% control | 3 |

Plant species in the table are identified by the same code letters used in the previous example.

TABLE III

| Compound of Example No. | WAT | kg/h | A | B | C | D | E | F | G | H | I | J | K |
|---|---|---|---|---|---|---|---|---|---|---|---|---|---|
| 1 | 2 | 11.2 | 2 | 0 | 0 | 0 | 0 | 0 | 0 | 0 | 0 | 0 | 0 |
| 3 | 2 | 11.2 | 0 | 0 | 0 | 0 | 0 | 1 | 0 | 1 | 1 | 0 | 0 |
| 4 | 2 | 11.2 | 3 | 0 | 0 | 0 | 0 | 0 | 0 | 0 | 0 | 0 | 0 |
| 5 | 4 | 11.2 | 3 | 0 | 0 | 0 | 2 | 0 | 0 | 0 | 1 | 0 | 0 |
| 6 | 2 | 11.2 | 3 | 0 | 0 | 0 | 0 | 0 | 0 | 3 | 1 | 0 | 0 |
| 7 | 4 | 11.2 | 3 | 0 | 0 | 0 | 1 | 0 | 0 | 0 | 1 | 1 | 0 |
| 8 | 2 | 11.2 | 1 | 0 | 0 | 0 | 0 | 0 | 1 | 1 | 0 | 1 | 0 |
| 9 | 2 | 11.2 | 3 | 0 | 0 | 0 | 0 | 0 | 0 | 0 | 0 | 0 | 0 |
| 11 | 2 | 11.2 | 2 | 0 | 0 | 1 | 1 | 1 | 3 | 2 | 3 | 1 | 1 |

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

From Table III, it can be seen that the pre-emergent herbicidal activity demonstrated some selectivity.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor such as ethanol mercaptan, sodium thiosulfate, dodecylmono or dimercaptan or anti-foaming agent such as a dimethylpolysiloxane, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

The following list gives some specific herbicidal compositions of this invention. It is to be realized that the solvents and surfactants are interchangeable in the composition.

| | | |
|---|---|---|
| 1. | N—[bis(pyrrolidino)phosphinothioyl-methyl]glycine, 2-ethoxy ethyl ester | 95 Parts |
| | Methanol | 5 Parts |
| 2. | N—[bis(N—methyl-N—benzylamino)phosphinothioylmethyl]glycine, octyl ester | 95 Parts |
| | Ethoxylated nonyl phenol | 5 Parts |
| 3. | N—[bis(morpholino)phosphinothioyl-methyl]glycine, isopropyl ester | 90 Parts |
| | Isopropanol | 10 Parts |
| 4. | N—[bis(dimethylamino)phosphinothioylmethyl]glycine, ethyl ester | 90 Parts |
| | Ethoxylated octyl phenol | 10 Parts |
| 5. | N—[bis(2,2-dimethylhydrazino)phosphinothioylmethyl]glycine, ethyl ester | 90 Parts |
| | Chloroform | 5 Parts |
| | Ethoxylated dinonyl phenol | 5 Parts |
| 6. | N—[bis(ethylamino)phosphinothioyl-methyl]glycine, ethyl ester | 75 Parts |
| | Butanol | 25 Parts |
| 7. | N—[bis(pyrrolidino)phosphinothioyl-methyl]glycine, ethyl ester | 75 Parts |
| | Ethoxylated oleyl alcohol | 25 Parts |
| 8. | N—[bis(sec-butylamino)phosphino-thioylmethyl]glycine, butyl ester | 75 Parts |
| | Acetonitrile | 15 Parts |
| | Ethoxylated cocamine | 10 Parts |
| 9. | N—[bis(pryrrolidino)phosphinothioyl-methyl]glycine, 2-ethoxyethyl ester | 75 Parts |
| | 1,2-Dimethoxyethane | 20 Parts |
| | Ethoxylated tallow amaine | 5 Parts |
| 10. | N—[bis(N—methyl-N—benzylamino)phosphinothioylmethyl]glycine, octyl ester | 50 Parts |
| | Dimethylformamide | 50 Parts |
| 11. | N—[bis(morpholino)phosphinothioyl-methyl]glycine, isopropyl ester | 50 Parts |
| | Isopropyl dodecylbenzene sulfonate | 50 Parts |
| 12. | N—[bis(dimethylamino)phosphinothioyl-methyl]glycine, isopropyl ester | 50 Parts |
| | Dimethylsulfoxide | 40 Parts |
| | Ethoxylated soybeanamine | 10 Parts |
| 13 | N—[bis(ethylamino)phosphinothioyl-methyl]glycine, ethyl ester | 50 Parts |
| | γ-butyrolactone | 25 Parts |
| | Triethanolamine dodecylbenzene sulfonate | 25 Parts |
| 14. | N—[bis(cyclohexylamino)phosphino-thioylmethyl]glycine, ethyl ester | 50 Parts |
| | 1,1,1-Trichloroethane | 42 Parts |
| | Ethoxylated nonyl phenol | 8 Parts |
| 15. | N—[bis(isopropylamino)phosphino-thioylmethyl]glycine, ethyl ester | 25 Parts |
| | Chloroform | 75 Parts |
| 16. | N—[bis(piperidineamino)phosphino-thioylmethyl]glycine, ethyl ester | 25 Parts |
| | Chloroform | 70 Parts |
| | Ethoxylated tallow amine | 5 Parts |
| 17. | N—[bis(diallylamino)phosphinothioyl-methyl]glycine, ethyl ester | 25 Parts |
| | 1,1,1-Trichloroethane | 74 Parts |
| | Ethoxylated oleyl alcohol | 1 Part |
| 18. | N—[bis(2,2-dimethylhydrazino)phosphinothioylmethyl]glycine, ethyl ester | 25 Parts |
| | Chloroform | 68 Parts |
| | Ethoxylated dinonyl phenol | 7 Parts |
| 19. | N—[bis(cyclohexylamino)phosphino-thioylmethyl]glycine, ethyl ester | 10 Parts |
| | Chloroform | 90 Parts |
| 20. | N—[bis(pyrrolidino)phosphinothioyl-methyl]glycine, ethyl ester | 10 Parts |
| | Methanol | 80 Parts |
| | Polyoxypropylene - polyoxyethylene block copolymer | 10 Parts |
| 21. | N—[bis(sec-butylamino)phosphino-thioylmethyl]glycine, butyl ester | 10 Parts |
| | Ethanol | 88 Parts |
| | Polyoxyethylene (20) sorbitan-monolaurate | 2 Parts |
| 22. | N—[bis(pyrrolidino)phosphinothioyl-methyl]glycine, 2-ethoxyethyl ester | 10 Parts |
| | Isopropanol | 72 parts |
| | Polyoxyethylene sorbitanmonooleate | 18 Parts |
| 23. | N—[bis(N—methyl-N—benzylamino)phos- | 5 Parts |

| | | |
|---|---|---|
| -continued | | |
| phinothioylmethyl]glycine, octyl ester | | |
| Dimethylformamide | 95 | Parts |
| 24. N—[bis(morpholino)phosphinothioyl-methyl]glycine, isopropyl ester | 5 | Parts |
| Acetonitrile | 90 | Parts |
| Ethoxylated tallow amine | 5 | Parts |
| 25. N—[bis(dimethylamino)phosphinothioyl-methyl]glycine, ethyl ester | 5 | Parts |
| Ethanol | 94 | Parts |
| Ethoxylated tallow amine | 1 | part |
| 26. N—[bis(ethylamino)phosphinothioyl-methyl]glycine, ethyl ester | 5 | Parts |
| Isopropanol | 80 | Parts |
| Ethoxylated cocoamine | 15 | Parts |

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 56.0 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula

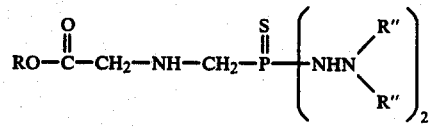

wherein
R is a member of the group consisting of alkyl of 1 to 8 carbon atoms, chloroalkyl of from 1 to 4 carbon atoms and from 1 to 3 chlorine atoms and alkoxyalkyl containing from 3 to 7 carbon atoms; and
R" is hydrogen or a $C_1$ to $C_4$ alkyl.

2. A herbicidal composition comprising a herbicidally effective amount of a compound of claim 1 and an inert diluent.

3. A herbicidal method which comprises applying to the plant or the plant locus a herbicidally effective amount of a compound of claim 1.

4. A compound of claim 1 wherein R is ethyl.

5. A herbicidal composition of claim 2 wherein R is ethyl.

6. A herbicidal method which comprises applying to the plant or the plant locus a herbicidally effective amount of a compound of claim 1 wherein R is ethyl.

7. A compound according to claim 1 having the formula:

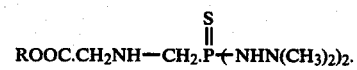

8. A herbicidal composition according to claim 2 comprising a compound according to claim 7.

9. A herbicidal method according to claim 3 which comprises applying to the plant or the plant locus a herbicidally effective amount of a compound of claim 7.

* * * * *